United States Patent
Morgret et al.

(10) Patent No.: US 11,193,919 B2
(45) Date of Patent: Dec. 7, 2021

(54) METHODS FOR IDENTIFYING CARBON DERIVED FROM NATURAL SOURCES

(71) Applicant: WM. WRIGLEY JR. COMPANY, Chicago, IL (US)

(72) Inventors: Leslie Morgret, Northborough, MA (US); David Phillips, Downers Grove, IL (US); Philip Urnezis, Chicago, IL (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 747 days.

(21) Appl. No.: 16/063,317

(22) PCT Filed: Dec. 16, 2016

(86) PCT No.: PCT/US2016/067160
§ 371 (c)(1),
(2) Date: Jun. 18, 2018

(87) PCT Pub. No.: WO2017/116753
PCT Pub. Date: Jul. 6, 2017

(65) Prior Publication Data
US 2020/0271633 A1 Aug. 27, 2020

Related U.S. Application Data

(60) Provisional application No. 62/273,514, filed on Dec. 31, 2015.

(51) Int. Cl.
*G01N 33/02* (2006.01)
*G01N 1/40* (2006.01)
*G01N 30/06* (2006.01)
*G01N 30/12* (2006.01)

(52) U.S. Cl.
CPC ........... *G01N 33/02* (2013.01); *G01N 1/4055* (2013.01); *G01N 30/06* (2013.01); *G01N 2001/4061* (2013.01); *G01N 2030/062* (2013.01); *G01N 2030/121* (2013.01)

(58) Field of Classification Search
CPC ........ G01N 33/02; G01N 30/14; G01N 30/06; G01N 2030/121; G01N 2030/062; G01N 1/4055; G01N 2001/4061
See application file for complete search history.

(56) References Cited

U.S. PATENT DOCUMENTS

| 2009/0282004 A1 | 11/2009 | Williams |
| 2012/0322159 A1 | 12/2012 | Kriegel |
| 2016/0096954 A1* | 4/2016 | Heo ...................... C08F 212/10 525/72 |

FOREIGN PATENT DOCUMENTS

WO WO2011036139 A1 3/2011

OTHER PUBLICATIONS

Tisdale, Evgenia, et al. "Method development for compositional analysis of low molecular weight poly(vinyl acetate) by matrix-assisted/laser desorption-mass spectrometry and its application to analysis of chewing gum" Analytica Chimica Acta 820 (2014) 92-103. (Year: 2014).*
ASTM International, Standard Test Methods for Determining the Biobased Content of Solid, Liquid, and Gaseous Samples Using Radiocarbon Analysis, ASTM International Standard, Feb. 3, 2010, pp. 698-712, ASTM D6866-08.
Gasco-Lopez A I et al., Development and Validation Of A High-Performance Liquid Chromatography Method for the Determation of Cold Relif Ingredients in Chewing Gum, J. Chromatography A, Jul. 18, 1997, pp. 179-185, 775(1-2), Elsevier, Amsterdam, NL.

* cited by examiner

*Primary Examiner* — Paul M. West

(57) ABSTRACT

Methods for identifying carbon derived from natural sources in a confectionary product are presented. Methods include separating, extracting and carbon dating components of a confectionary product, e.g., chewing gum or chewing gum base.

13 Claims, No Drawings

METHODS FOR IDENTIFYING CARBON DERIVED FROM NATURAL SOURCES

CROSS-REFERENCE TO RELATED APPLICATION

This application claims priority to U.S. Application No. 62/273,514, filed Dec. 31, 2015, the contents of which are hereby incorporated in their entirety.

FIELD

The presently disclosed subject matter relates to methods for identifying carbon derived from natural sources in a confectionary product.

BACKGROUND

Chewing gum and chewing gum base are complex multi-component mixtures which include, but are not limited to, synthetic resins, natural resins, synthetic rubbers, fats, and fillers. Currently there is interest in delivering green or bio-based chewing gum products. These products can contain ingredients sourced from natural or renewable resources. The resources can be identified based on the age of their carbon content, calculated as the length of time since that carbon was incorporated into organic molecules by a living organism, e.g., a plant. For example, renewable resources, derived from agricultural crops, typically have an age ranging from a few days to a few years. Classically, chewing gum bases have been produced from organic compounds derived from petroleum. Based on the age of their carbon content, these compounds typically have an age of >50,000 years.

Some chewing gum products that identify as "natural" may contain a mixture of petroleum based and agro-based ingredients. However, due to the large number of ingredients, including inorganic fillers, it can be difficult to separate the chewing gum or chewing gum base into individual components to determine the sources by carbon dating. Additionally, inorganic fillers can affect the carbon dating of the sample. The presently disclosed subject matter addresses this problem.

SUMMARY OF THE INVENTION

The presently disclosed subject matter is directed to methods for identifying carbon derived from natural sources in chewing gum or chewing gum base, comprising pre-treating the chewing gum or chewing gum base to separate the chewing gum or chewing gum base into constituent parts. The method can further include detecting presence of carbon isotopes in each constituent part. The method can also include quantifying each detected carbon isotope and calculating relative ratios of the detected carbon isotopes; and determining the sources of carbon based on the relative ratios.

In certain embodiments, pre-treating the chewing gum or chewing gum base includes extracting and/or separating volatiles, organic materials, non-polar organic materials, inorganic fillers and/or polar organic materials.

In certain embodiments, pre-treating the chewing gum or chewing gum base is conducted using one or more separation techniques selected from the group consisting of gas chromatography, liquid chromatography, gel permeation chromatography, thermal gravimetric analysis, liquid-liquid extraction, solid-liquid extraction, solvent-extraction separation and combinations thereof.

In certain embodiments, pre-treating the chewing gum or chewing gum base includes solvent-extraction separation to remove inorganic fillers.

In certain embodiments, the solvent-extraction separation comprises a) using a soxlet to extract organic material from the chewing gum or chewing gum base with lipophilic solvent, and b) removing the solvent to obtain and separate organic material and inorganic fillers.

In certain embodiments, the inorganic fillers include calcium carbonate, talc, magnesium carbonate, ground limestone, silicate types such as magnesium and aluminum silicate, clay, alumina, titanium oxide, mono-, di- and tri-phosphate, and combinations thereof.

In certain embodiments, the pre-treating comprises collecting volatiles with a cold trap while heating the chewing gum or chewing gum base. The pre-treating can also include extracting organic material with lipophilic solvent. The pre-treating can further include removing the lipophilic solvent to obtain organic materials present in the chewing gum or chewing gum base; and separating the organic materials into polar and non-polar organic materials.

In certain embodiments, the polar organic materials include polylactides, polyvinyl acetate, polyglycolides, polycaprolactone (fossil-based), PLA/PGA/PCL block copolymers, polyhydroxybutyrate, cellulose acetate, thermoplastic starch, pluronics (PEO-PPO block polymers), hydrogel polymers, emulsifiers, and/or glycerol mono laurate. In certain embodiments, the non-polar organic materials include polyisobutylene, styrene-butadiene rubber, butyl rubber, block copolymers, polyacrylates, waxes, polyethylene, natural rubbers and latexes such as chicle, and/or guayule.

In certain embodiments, the detecting includes measuring the $^{14}C$, $^{13}C$, and $^{12}C$ present in each constituent part by one or more carbon dating methods.

In certain embodiments, the detecting is accurate at carbon levels of 3 mol/mol % or greater in each constituent part.

In certain embodiments, the one or more carbon dating methods is selected from the group consisting of modified Geiger counter, gas proportioned counter, liquid scintillation counting; accelerator mass spectrometry and combinations thereof.

In certain embodiments, the pre-treating comprises collecting volatiles with a cold trap while heating the chewing gum or chewing gum base. The pre-treating can also include extracting organic materials from the chewing gum or chewing gum base with lipophilic solvent.

The pre-treating can further include separating the organic materials into polar and non-polar organic materials. The pre-treating can further include extracting hydrophilic organic materials from the chewing gum or chewing gum base with hydrophilic solvent; and extracting dye from the chewing gum or chewing gum base.

The foregoing has outlined broadly the features and technical advantages of the present disclosure in order that the detailed description that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

DETAILED DESCRIPTION

As noted above, there remains a need in the art for methods for identifying carbon derived from natural sources in a confectionary product, e.g., chewing gum or chewing gum base. In certain embodiments, the method provides for separation and extraction of inorganic materials from organic materials to increase accuracy of carbon dating.

1. Definitions

The terms used in this specification generally have their ordinary meanings in the art, within the context of this disclosed subject matter and in the specific context where each term is used. Certain terms are discussed below, or elsewhere in the specification, to provide additional guidance to the practitioner in describing the compositions and methods of the disclosed subject matter and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value.

As used herein, "ppm" means parts-per-million and is a weight relative parameter. A part-per-million is a microgram per gram, such that a component that is present at 10 ppm is present at 10 micrograms of the specific component per 1 gram of the aggregate mixture.

As used herein, the term "chewing gum" refers to a confection which contains a water insoluble elastic gum base intended for chewing. The term as used herein includes bubble gum and confectionery products containing chewing gum. In certain embodiments, chewing gum forms include, but are not limited to, tablets, sticks, solid balls, hollow balls, cut and wrap, and pellets or pillows. Unless otherwise specified, all percentages used herein are weight percents. As used herein, chewing gum contains a water insoluble base portion and a water-soluble bulk portion.

As used herein, "filler" refers to materials incorporated into a chewing gum which are not soluble and remain in chewing gum cud after chewing. Inorganic fillers include, but are not limited to, calcium carbonate, magnesium carbonate, talc, ground limestone, silicate types such as magnesium and aluminum silicate, clay, alumina, titanium oxide, mono-, di- and tri-phosphate, and combinations thereof. Organic fillers include, but are not limited to cellulose polymers such as wood, natural fibers, including inulin and cotton, rice hulls, and corn husks. Carbon-containing inorganic fillers, most notably calcium carbonate, may contain ancient carbon greater than 50,000 years old. However, unlike petroleum-derived components, the sources of these fillers are considered inexhaustible for practical purposes.

As used herein, "age of carbon", refers to length of time since that carbon was incorporated into organic molecules by a living organism, most typically a plant. For example, organic compounds derived from agricultural crops typically have an age ranging from a few days to perhaps a few years. Conversely, petroleum is produced when plant material is buried and subjected to heat and pressure over a period of millions of years. Therefore, organic compounds derived from petroleum typically have an age of >50,000 years.

As used herein, "renewable" or "agro-based" carbon and chewing gum components refers to organic compounds derived from agricultural sources such as, but not limited to, crops, forests, and shrubbery, typically having an age ranging from a few days to perhaps a few years. The terms "natural" and "bio-based" may also be used interchangeably. The percentage of bio-based carbon in a sample may be calculated by various methods, including but not limited to, accelerator mass spectrometry (AMS).

As used herein, "petroleum based" or "ancient source" carbon and chewing gum components refers to organic compounds derived from petroleum or other fossil carbon sources such as natural gas and coal, typically having an age of carbon >50,000 years by radiocarbon dating.

2. Chewing Gum

Chewing gum can be produced using conventional procedures and equipment and suitable additional components known in the art, for example, as described by U.S. Publication Nos. 2013/0156885 and U.S. 2005/0202118, each of which is incorporated by reference in its entirety herein.

A chewing gum center composition or other chewing gum compositions contain a chewable gum base portion, which is water-insoluble, and forms a cud upon chewing, and a water-soluble bulk portion. Flavors which can be water insoluble are normally considered part of the water soluble bulk portion. The water-soluble portion dissipates with a portion of the flavor over a period of time during chewing. The gum base portion is retained in the mouth throughout the chew until it is expectorated.

In certain embodiments, the insoluble gum base comprises elastomers, elastomer solvents, plasticizers, waxes, emulsifiers and/or inorganic fillers. Synthetic resins, such as polyvinyl acetate, can also be included. In certain embodiments, synthetic resins can include but are not limited to, polyvinyl acetate, polyvinyl laureate, polyvinyl alcohol and polyvinyl pyrrolidone.

Non-limiting examples of elastomers can include polyisobutylene, butyl rubber, (isobutylene-isoprene copolymer) and styrene butadiene rubber, as well as natural latexes such as chicle. In certain embodiments, elastomer solvents can include resins such as terpene resins. In certain embodiments, the plasticizers are fats and oils, including but not limited to, tallow, hydrogenated and partially hydrogenated vegetable oils, and cocoa butter.

In certain embodiments, the waxes include, but are not limited to paraffin, microcrystalline and natural waxes such as beeswax, candelilla wax, and carnauba wax.

In certain embodiments, the inorganic fillers can include, but are not limited to calcium carbonate, magnesium carbonate, talc, ground limestone, silicate types such as magnesium and aluminum silicate, clay, alumina, titanium oxide, mono-, di- and tri-phosphate, and combinations thereof. Organic fillers can include, but are not limited to, natural fibers, including cellulose polymers, such as wood and cotton, inulin, rice hulls, and corn husks.

In certain embodiments, the chewing gum further contains one or more flavor components that are derived from artificial or natural sources or combinations thereof. In certain embodiments, the chewing gum can contain sugar, or may be sugar-free.

In certain embodiments, the chewing gum further contains one more coloring agents. In certain embodiments, the coloring agents can be food quality dyes.

Each of these constituent parts of chewing gum and chewing gum base can be sourced from renewable sources (also referred to as agricultural products) or petroleum based sources (also referred to as ancient sources), or in the case of fillers, mined as minerals. While the final product is essentially identical regardless of the source, the products can have carbon content of different ages, calculated as the length of time since that carbon was incorporated into organic molecules by a living organism. For example, chewing gum base comprising synthetic resin can be examined to find the age of the carbon in the synthetic resin to determine whether the resin was naturally sourced or petroleum sourced. Other chewing gum components, including but not limited to, polymers, elastomers, emulsifiers, oil, softeners and waxes all contain carbon which can be carbon dated to determine the source, i.e., natural versus petroleum based, of the constituent parts.

In certain embodiments, inorganic fillers can comprise carbon. In certain embodiments, inorganic fillers must be extracted from the chewing gum or chewing gum base before determining the carbon content of the other constituent parts. Alternatively, the inorganic fillers can be extracted and the age of their carbon content determined independently of the organic constituent parts.

3. Methods of Analysis

The presently disclosed subject matter includes methods of separating a chewing gum or chewing gum base into its constituent parts and evaluating the source of carbon in each part. In certain embodiments, the method can include pre-treating the chewing gum or chewing gum base to separate the chewing gum or chewing gum base into constituent parts and detecting presence of carbon isotopes in each constituent part. The method can also include quantifying each detected carbon isotope and calculating relative ratios of the detected carbon isotopes. The method can further include determining the sources of carbon based on the relative ratios and determining the total bio-based content of a constituent part.

3.1 Separation

The presently disclosed subject matter includes methods of pre-treating the chewing gum or chewing gum base to separate the chewing gum or chewing gum base into each of the constituent parts as described previously.

In certain embodiments, the chewing gum or chewing gum base is pre-treated by separating and extracting volatiles, organic materials, inorganic materials, non-polar organic materials and/or polar organic materials.

In certain embodiments, pre-treating includes collecting volatiles with a cold trap while heating the confectionary product. The pre-treating can further include extracting organic material with lipophilic solvent and removing the lipophilic solvent to obtain organic materials present in the confectionary product. The pre-treating can also include separating the organic materials into polar and non-polar organic materials.

In further embodiments, the pre-treating can include, but is not limited to, collecting volatiles with a cold trap while heating the chewing gum or chewing gum base and extracting organic materials from the chewing gum or chewing gum base with lipophilic solvent. The pre-treating can also include separating the organic materials into polar and non-polar organic materials and extracting hydrophilic organic materials from the chewing gum or chewing gum base with hydrophilic solvent. The pre-treating can also include extracting dye from the chewing gum or chewing gum base. In certain embodiments a chewing gum is pre-treated. In other embodiments, a chewing gum base is pretreated.

In certain embodiments, the polar organic materials include polylactides, polyvinyl acetate, polyglycolides, polycaprolactone (fossil-based), PLA/PGA/PCL block copolymers, polyhydroxybutyrate, cellulose acetate, thermoplastic starch, pluronics (PEO-PPO block polymers), hydrogel polymers, emulsifiers, and/or glycerol mono laurate. In certain embodiments, the non-polar organic materials include polyisobutylene, styrene-butadiene rubber, butyl rubber, block copolymers, polyacrylates, styrene-diene copolymers, poly(cis-1,4 isoprene), waxes, polyethylene, natural rubbers and latexes such as chicle, and guayule.

In certain embodiments, any inorganic filler in the chewing gum or chewing gum base must be extracted. Any carbon present in the inorganic filler can give a false identification of the carbon source of the other constituent parts. For example, the inorganic filler calcium carbonate can be produced by a reaction which includes carbon dioxide as a reactant. The precipitated calcium carbonate therefore contains the same carbon from the atmosphere as plants and agro-based organic materials. The age of the carbon in the precipitated calcium carbonate would therefore be appear younger than mined calcium carbonate whose carbon was sequestered thousands to millions of years ago.

In certain embodiments, the inorganic filler is talc and does not contain any carbon. Therefore, talc should not affect the identification of the carbon source of the other constituent parts.

In embodiments, the inorganic filler is extracted through use of solvent-extraction separation. In certain embodiments, solvent-extraction separation utilizes a soxlet. A soxlet allows extracts any organic material from the chewing gum or chewing gum base and leaves behind inorganic fillers. Separation and identification of the constituent parts of the organic material can then proceed.

In certain embodiments, separation techniques are selected from the group consisting of gas chromatography, liquid chromatography, gel permeation chromatography, thermal gravimetric analysis, liquid-liquid extraction, solid-liquid extraction, solvent-extraction separation and combinations thereof. Solvents for use in the separations and extractions include any solvent knowing in the art for separating volatiles, organic materials, inorganic materials, non-polar organic materials and/or polar organic materials.

Non-polar organic solvents include, but are not limited to, hexanes, octanes, and iso-octanes. Polar organic solvents include, but are not limited to, acetonitrile, methanol, ethanol, acetone.

In certain embodiments, extraction and separation techniques are either an in-situ or offline method.

3.2 Carbon Dating

The presently disclosed subject matter includes methods of evaluating the source of carbon, i.e., agro-based or petroleum based, in each separated constituent part. The source of carbon can be determined by quantifying each detected carbon isotope and calculating relative ratios of the detected carbon isotopes. The method further includes determining the sources of carbon based on the relative ratios.

The most prevalent naturally occurring isotopes of carbon include $^{14}C$, $^{13}C$, and $^{12}C$. $^{14}C$ is unstable and radioactive. The decay rate of $^{14}C$ is constant, spontaneous and has a half-life of about 5730 years. The age of an organic sample can be determined by knowing the amount of $^{14}C$ in the organic material when life ceased and measuring the amount of $^{14}C$ in the material currently, against relevant standards. Petroleum-based materials are considered greater than 50,000 years old based on carbon dating. Agro-based materials, or natural materials, are less than 50 years old based on carbon dating. Each constituent part of chewing gum and chewing gum base can be evaluated in this manner.

In certain embodiments detecting carbon isotopes in chewing gum or chewing gum base includes measuring the $^{14}C$, $^{13}C$, and $^{12}C$ present in each constituent part by one or more carbon dating methods.

In certain embodiments, the one or more carbon dating methods is selected from, but not limited to, the group consisting of modified Geiger counter, gas proportioned counter, liquid scintillation counting; accelerator mass spectrometry (AMS) and combinations thereof.

In certain embodiments, the carbon dating method measures beta particles over time against a blank and standard to enable calculation of the age of the sample by $^{14}C$ radioactive decay.

In certain embodiments, AMS can include separating the carbon of interest using one of the techniques discussed above, converting to graphite and placing into a sputter ion source of an accelerator for measurement. In certain embodiments, AMS can detect carbon levels of 4% or greater. In certain embodiments, the detecting is accurate at carbon levels of 3 mol/mol % or greater in each constituent part. In certain embodiments, the AMS method is ASMT D6866 standard method.

In certain embodiments, AMS can be used to calculate the percent of bio-based content of typical ingredients used in gum. For example, in certain embodiments, chicle rubber, a natural rubber, is calculated to be 100% bio-based using AMS. By contrast, in certain embodiments, poly(vinyl acetate), a synthetic rubber, is calculated to be 0% bio-based using AMS. In certain embodiments, a constituent part, e.g., a gum base can comprise a combination of bio-based and petroleum based materials, resulting in percentages of more than 0 but less than 100 by AMS.

In certain embodiments, each constituent part can be carbon dated using the same or a different carbon dating method.

In further embodiments, other confectionary products and ingredients can be evaluated by the presently disclosed methods.

EXAMPLES

The presently disclosed subject matter will be better understood by reference to the following Examples, which are provided as exemplary of the disclosed subject matter, and not by way of limitation.

Example 1—Gum Base

In this Example, a gum base is analyzed to determine whether the component parts are derived from natural sources.

The procedure is as follows:
1. Collect volatiles with cold trap while sample is gently heated.
2. Test volatiles to determine if they are derived from petroleum sources by checking their age.
3. Using a soxlet, extract organic material from sample, after heating, with lipophilic solvent.
4. Remove solvent to obtain gum base's organic material.
5. Add combination of non-polar organic solvent and polar organic solvent to this organic material.
6. Separate the non-polar organic solvent from the polar organic solvent.
7. Remove non-polar organic solvent to obtain gum base's non-polar organic material.
8. Test non-polar organic materials to determine if they are derived from petrochemical sources by checking their age.
9. Remove the polar organic solvent to obtain gum base's polar organic material.
10. Test polar organic materials to determine if they are derived from petrochemical sources by checking their age.

Example 2—Chewing Gum

In this Example, a chewing gum is analyzed to determine whether the component parts are derived from natural sources.

The procedure is as follows:
1. Collect volatiles with cold trap while sample is gently heated.
2. Test volatiles to determine if they are derived from petroleum sources by checking their age.
3. Using a soxlet, extract organic material from sample, after heating, with lipophilic solvent.
4. Remove solvent to obtain chewing gum's lipophilic organic material.
5. Add combination of non-polar organic solvent and polar organic solvent to this organic material.
6. Separate the non-polar organic solvent from the polar organic solvent.
7. Remove non-polar organic solvent to obtain chewing gum's non-polar organic material.
8. Test non-polar organic materials to determine if they are derived from petrochemical sources by checking their age.
9. Remove the polar organic solvent to obtain chewing gum's polar organic material.
10. Test polar organic materials to determine if they are derived from petrochemical sources by checking their age.
11. Dry residual solids.
12. Dissolve chewing gum's hydrophilic organic material from residual solids with a hydrophilic solvent.
13. Separate solids.
14. Wash solids multiple times with hydrophilic solvent.
15. Combine wash hydrophilic solvent with extraction hydrophilic solvent.

16. Remove hydrophilic solvent to obtain chewing gum's hydrophilic organic material.

17. Test hydrophilic organic materials to determine if they are derived from petrochemical sources by checking their age.

18. Add aqueous caustic solution to solids to release dye from lakes.

19. Separate dye from aqueous caustic with multiple extractions of organic solvent.

20. Remove organic solvent to obtain dye.

21. Test dyes to determine if they are derived from petrochemical sources by checking their age.

From there, organic samples are either combusted (900° C.) or reacted directly with cupric oxide (900° C.) to generate carbon dioxide ($CO_2$) gas. On the other hand, organics such as those from $CaCO_3$ in the filler portion of the sample (the ash) are acid hydrolyzed to $CO_2$ gas as well. If no organics exist, such as the case for pure talc, then no $CO_2$ gas will evolve. Any mixture in between shall evolve a fraction of the $CO_2$ gas. From there, $CO_2$ from each fraction is tested independently to determine their effective age. This is done by first cryogenically purifying the $CO_2$ gas using a series of dry ice/methanol (−79° C.) and nitrogen/pentane (−129° C.) cold traps to remove impurities. This $CO_2$ is then converted to graphite via the reaction shown in Equation 1. Finally, a series of vacuum purges with purified Argon gas is completed to prepare sample for AMS counting. In AMS, graphite is ionized, ions are selected and separated with a series of electric and magnetic fields, respectively, and $^{12}C$, $^{13}C$, and $^{14}C$ particles are identified use spectrometric detector.

$$CO_2(g)+2H_2(g) \rightarrow C(s)+2H_2O(l)(Co,@\sim 600° C.) \quad (1)$$

Example 3—ASM Testing of Typical Gum Base Ingredients

In this Example, typical ingredients used in gum base were analyzed to determine bio-based content baselines. The results are summarized in Table 1.

TABLE 1

Summary of Material Testing Results (AMS)

| Classification | Material | Results | Purpose |
|---|---|---|---|
| Synthetic Resin | Poly(vinyl acetate) | 0% | To demonstration the bio-based content of typical ingredients used in gum |
| Synthetic Rubber | Butyl Rubber | 1% | |
| Natural Rubber | Chicle Rubber | 100% | |
| Natural Resin | Glycerol Rosin Ester | 100% | |
| Natural Resin | Terpene Resin | 100% | |
| Fat | Fats | 100% | |
| Gum Base | Base A | 63% | To baseline accuracy of the method when used with gum base |
| | Base B | 79% | |
| | Base C | 100% | |

As shown by Table 1 not all ingredients are naturally-sourced and separation/extraction techniques are needed to determine the natural or petroleum gum base fraction. Therefore, the base compositions were individually prepared. The compositions are summarized in Table 2.

TABLE 2

Base Compositions

| Ingredients | Base A (wt %) | Base B (wt %) | Base C (wt %) |
|---|---|---|---|
| Synthetic Rubbers | 13 | 11 | 0 |
| Natural Rubbers | 0 | 0 | 100 |
| Synthetic Resins | 28 | 24 | 0 |
| Natural Resins | 25 | 23 | 0 |
| Fillers | 10 | 21 | 0 |
| Fats | 20 | 18 | 0 |
| Emulsifiers | 4 | 3 | 0 |
| Antioxidants | <1 | <1 | 0 |

Table 2 indicates that it is not easy to determine the bio-based content of a gum base formulation based on weight fractions alone. A prediction can be made based on carbon fraction which is then confirmed with AMS methodology.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:

1. A method for identifying carbon derived from natural sources in chewing gum or chewing gum base, comprising:
   a) pre-treating the chewing gum or chewing gum base to separate the chewing gum or chewing gum base into constituent parts;
   b) detecting presence of carbon isotopes in each constituent part based upon when life of the natural sources ceased;
   c) quantifying each detected carbon isotope and calculating relative ratios of the detected carbon isotopes; and
   d) determining if the sources of carbon are derived from petrochemical sources based on the relative ratios.

2. The method of claim 1, wherein the pre-treating the chewing gum or chewing gum base includes extracting and/or separating volatiles, organic materials, non-polar organic materials, inorganic fillers and/or polar organic materials.

3. The method of claim 2, wherein pre-treating the chewing gum or chewing gum base is conducted using one or more separation techniques selected from the group consisting of gas chromatography, liquid chromatography, gel permeation chromatography, thermal gravimetric analysis, liquid-liquid extraction, solid-liquid extraction, solvent-extraction separation and combinations thereof.

4. The method of claim 2, wherein pre-treating the chewing gum or chewing gum base includes solvent-extraction separation to remove inorganic fillers.

5. The method of claim 1, wherein the pre-treatment comprises solvent-extraction separation comprising a) using a soxlet to extract organic material from the chewing gum or chewing gum base with lipophilic solvent, and b) removing the solvent to obtain the separate organic material and inorganic fillers.

6. The method of claim 5, wherein the inorganic fillers are selected from the group consisting of calcium carbonate, talc, magnesium carbonate, ground limestone, silicate types such as magnesium and aluminum silicate, clay, alumina, titanium oxide, mono-, di- and tri-phosphate, and combinations thereof.

7. The method of claim 1, wherein the pre-treating comprises:
   a) collecting volatiles with a cold trap while heating the chewing gum or chewing gum base;
   b) extracting organic material with lipophilic solvent;
   c) removing the lipophilic solvent to obtain organic materials present in the chewing gum or chewing gum base; and
   d) separating the organic materials into polar and non-polar organic materials.

8. The method of claim 7, wherein the polar organic materials are selected from the group consisting of polylactides, polyvinyl acetate, polyglycolides, polycaprolactone (fossil-based), PLA/PGA/PCL block copolymers, polyhydroxybutyrate, cellulose acetate, thermoplastic starch, pluronics (PEO-PPO block polymers), hydrogel polymers, emulsifiers, and glycerol mono laurate.

9. The method of claim 7, wherein the non-polar organic materials are selected from the group consisting of polyisobutylene, styrene-butadiene rubber, butyl rubber, block copolymers, polyacrylates, waxes, polyethylene, natural rubbers and latexes such as chicle, and guayule.

10. The method of claim 1, wherein the detecting includes measuring the $^{14}C$, $^{13}C$, and $^{12}C$ present in each constituent part by one or more carbon dating methods.

11. The method of claim 10, wherein the detecting is accurate at carbon levels of 3 mol/mol % or greater in each constituent part.

12. The method of claim 10, wherein the one or more carbon dating methods is selected from the group consisting of modified Geiger counter, gas proportioned counter, liquid scintillation counting, accelerator mass spectrometry and combinations thereof.

13. The method of claim 1, wherein the pre-treating comprises:
   a) collecting volatiles with a cold trap while heating the chewing gum or chewing gum base;
   b) extracting organic materials from the chewing gum or chewing gum base with lipophilic solvent;
   c) separating the organic materials into polar and non-polar organic materials;
   d) extracting hydrophilic organic materials from the chewing gum or chewing gum base with hydrophilic solvent; and
   e) extracting dye from the chewing gum or chewing gum base.

* * * * *